United States Patent
Schulz et al.

(10) Patent No.: US 10,233,307 B2
(45) Date of Patent: Mar. 19, 2019

(54) DYE, FILLER MADE THEREFROM, COMPOSITIONS INCLUDING THE FILLER, AND METHOD OF DETERMINING DEGREE OF CURE OF SUCH COMPOSITIONS

(71) Applicant: 3M INNOVATIVE PROPERTIES COMPANY, St. Paul, MN (US)

(72) Inventors: Mark F. Schulz, Lake Elmo, MN (US); Michael S. Wendland, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 107 days.

(21) Appl. No.: 15/109,350

(22) PCT Filed: Dec. 19, 2014

(86) PCT No.: PCT/US2014/071683
§ 371 (c)(1),
(2) Date: Jun. 30, 2016

(87) PCT Pub. No.: WO2015/102966
PCT Pub. Date: Jul. 9, 2015

(65) Prior Publication Data
US 2016/0319105 A1 Nov. 3, 2016

Related U.S. Application Data

(60) Provisional application No. 61/921,644, filed on Dec. 30, 2013.

(51) Int. Cl.
| | |
|---|---|
| C08K 9/04 | (2006.01) |
| C08K 5/47 | (2006.01) |
| C09C 1/00 | (2006.01) |
| G01N 21/78 | (2006.01) |
| C09B 29/08 | (2006.01) |
| C09B 29/033 | (2006.01) |
| C09C 3/08 | (2006.01) |
| C09C 1/02 | (2006.01) |
| C09C 1/28 | (2006.01) |
| C09B 69/00 | (2006.01) |
| C08K 7/20 | (2006.01) |

(52) U.S. Cl.
CPC .............. *C08K 5/47* (2013.01); *C08K 7/20* (2013.01); *C08K 9/04* (2013.01); *C09B 29/0088* (2013.01); *C09B 29/0801* (2013.01); *C09B 29/0813* (2013.01); *C09B 29/0827* (2013.01); *C09B 29/0829* (2013.01); *C09B 69/008* (2013.01); *C09C 1/00* (2013.01); *C09C 1/021* (2013.01); *C09C 1/28* (2013.01); *C09C 3/08* (2013.01); *G01N 21/78* (2013.01)

(58) Field of Classification Search
CPC ..... C08L 67/06–67/07; C09B 29/0088; C08K 9/04–9/06; C08K 9/12
See application file for complete search history.

(56) References Cited

U.S. PATENT DOCUMENTS

| | | | |
|---|---|---|---|
| 2,466,963 | A | 4/1949 | Patrick |
| 2,789,958 | A | 4/1957 | Fettes |
| 2,891,942 | A | 6/1959 | Merian |
| 3,207,614 | A | 9/1965 | Canevari |
| 3,382,296 | A | 5/1968 | Tenquist |
| 3,390,121 | A | 6/1968 | Burford |

(Continued)

FOREIGN PATENT DOCUMENTS

| | | | |
|---|---|---|---|
| CN | 1865356 A | * | 11/2006 |
| CN | 101328320 | | 12/2008 |

(Continued)

OTHER PUBLICATIONS

Feigenbaum, A. Hydrogen bonding and retention on silica. J. Chem. Educ. 1986, 63, pp. 815-817. (Year: 1986).*
Freeman, H. S. et al. Purification process for synthetic dyes: Part 4—Flash chromatography. Dyes and Pigments, 1990, 12, 233-242. (Year: 1990).*
Machine Translation of CN1865356A. Nov. 22, 2006. (Year: 2006).*
Chen, "Synthesis and spectroscopic characterization of an alkoxysilane dye containing azo-benzothiazole chromophore for nonlinear optical applications", Dyes and Pigments, 2007, vol. 73, pp. 338-343.
Cojocariu, "Synthesis and optical storage properties of a novel polymethacrylate with benzothiazole azo chromophore in the side chain", Journal of Materials Chemistry, 2004, vol. 14, pp. 2909-2916.

(Continued)

*Primary Examiner* — Stephen R Rieth

(57) ABSTRACT

A compound represented by formula (I): and a treated filler having the compound on at least a portion of its surface. R is hydrogen or alkyl. X is alkylene, arylalkylene, or alkylarylene, each optionally interrupted by at least one of an ether, thioether, amine, amide, ester, thioester, carbonate, thiocarbonate, carbamate, thiocarbamate, urea, or thiourea, with alkylene optionally interrupted by arylene. W is hydroxyl, a sulfonic acid group, a phosphonic acid group, carboxylic acid group, —NHR$^1$, epoxy, or —Si(Y)$_x$(Z)$_{3-x}$. Y is alkyl, aryl, arylalkylenyl, or alkylarylenyl. Z is halide, hydroxyl, alkoxy aryloxy, acyloxy, polyalkyleneoxy, —O— covalently bonded to the surface of the filler, or —O bonded to another silicon atom, and x is 0 or 1. A composition including the treated filler, a method of making the treated filler, and a method of determining the degree of cure of a curable polymeric resin are also disclosed.

(I)

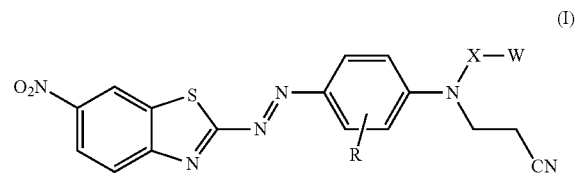

23 Claims, No Drawings

(56) References Cited

U.S. PATENT DOCUMENTS

| | | |
|---|---|---|
| 3,773,706 A | 11/1973 | Dunn, Jr. |
| 3,959,209 A * | 5/1976 | Lake ............... C08L 67/06 523/527 |
| 4,160,064 A | 7/1979 | Nodiff |
| 4,164,492 A | 8/1979 | Cooper |
| 4,165,425 A | 8/1979 | Bertozzi |
| 4,232,136 A | 11/1980 | Kovacsay |
| 4,241,166 A | 12/1980 | Klupfel |
| 4,366,307 A | 12/1982 | Singh |
| 4,370,428 A | 1/1983 | Danville |
| 4,440,681 A | 4/1984 | Tappe |
| 4,460,719 A | 7/1984 | Danville |
| 4,467,079 A | 8/1984 | Hechenberger |
| 4,488,992 A | 12/1984 | Yoshinaga |
| 4,507,407 A | 3/1985 | Kluger |
| 4,522,963 A | 6/1985 | Kecskemethy |
| 4,609,762 A | 9/1986 | Morris |
| 4,734,101 A | 3/1988 | Himeno |
| 4,980,414 A | 12/1990 | Naton |
| 5,028,456 A | 7/1991 | Naton |
| 5,225,472 A | 7/1993 | Cameron |
| 5,302,627 A | 4/1994 | Field |
| 5,373,036 A | 12/1994 | Parish |
| 5,387,488 A | 2/1995 | Kaneko |
| 5,456,947 A | 10/1995 | Parish |
| 5,610,243 A | 3/1997 | Vietti |
| 5,912,319 A | 6/1999 | Zook |
| 5,933,559 A | 8/1999 | Petisce |
| 5,958,584 A | 9/1999 | Petisce |
| 5,959,071 A | 9/1999 | DeMoss |
| 6,063,864 A | 5/2000 | Mathur |
| 6,162,842 A | 12/2000 | Freche |
| 6,172,179 B1 | 1/2001 | Zook |
| 6,444,725 B1 | 9/2002 | Trom |
| 6,447,708 B1 | 9/2002 | Thépot et al. |
| 6,455,158 B1 | 9/2002 | Mei |
| 6,465,544 B1 | 10/2002 | Bomal |
| 6,509,418 B1 | 1/2003 | Zook |
| 6,518,356 B1 | 2/2003 | Friese |
| 6,778,753 B2 | 8/2004 | Blomquist |
| 7,309,517 B2 | 12/2007 | Jones |
| 7,691,557 B2 | 4/2010 | Bachmann |
| 7,863,369 B2 * | 1/2011 | Bianchi ............ C08K 7/00 106/262 |
| 7,871,446 B2 | 1/2011 | Jordan |
| 2003/0027903 A1 | 2/2003 | Nwoko |
| 2003/0065069 A1 | 4/2003 | Wojciak |
| 2003/0139488 A1 | 7/2003 | Wojciak |
| 2003/0181546 A1 | 9/2003 | Hettich |
| 2006/0202158 A1 | 9/2006 | Chen |
| 2007/0021526 A1 | 1/2007 | He |
| 2008/0194766 A1 * | 8/2008 | Neri ............... C08J 3/22 525/240 |
| 2010/0311184 A1 | 12/2010 | Diwu |
| 2011/0171609 A1 | 7/2011 | Yang |
| 2012/0040103 A1 | 2/2012 | Keledjian |
| 2016/0041143 A1 | 2/2016 | Wendland |
| 2016/0319106 A1 | 11/2016 | Ye |

FOREIGN PATENT DOCUMENTS

| | | |
|---|---|---|
| CN | 103113759 | 5/2013 |
| EP | 1095985 | 5/2001 |
| EP | 1308477 | 10/2002 |
| GB | 1435077 | 5/1976 |
| JP | S44 9758 | 5/1969 |
| JP | 44-13389 | 6/1969 |
| JP | 44-20269 | 9/1969 |
| JP | 46-1351 | 1/1971 |
| JP | 50-69381 | 6/1975 |
| JP | 56-43358 | 4/1981 |
| JP | S56 91081 | 7/1981 |
| JP | 58-152055 | 9/1983 |
| JP | 59-27958 | 2/1984 |
| JP | 59-120612 | 7/1984 |
| JP | 61-200170 | 4/1986 |
| JP | 62-034958 | 2/1987 |
| JP | 8-108625 | 4/1996 |
| JP | H10-237335 | 8/1998 |
| JP | 2001-131436 | 5/2001 |
| JP | 2008-144103 | 6/2008 |
| WO | WO 1995-19379 | 7/1995 |
| WO | WO 2012-021781 | 2/2012 |
| WO | WO 2013-090988 | 6/2013 |
| WO | WO 2013-151893 | 10/2013 |
| WO | WO 2014-164103 | 10/2014 |

OTHER PUBLICATIONS

Peters, "Disperse Dyes: 4-Hetarylazo Derivatives from N-β-Cyanoethyl-N-β-Hydroxyethylaniline", Journal Chemical Technology Biotechnology 1992, vol. 53, pp. 301-308.

Peters, "Monoazo Disperse Dyes Derived from Nitro-2-Aminobenzothiazoles", Dyes and Pigments, 1995, vol. 28, pp. 151-164.

Sanchez, "Applications of advanced hybrid organic-inorganic nanomaterials: from laboratory to market", Chemical Society Reviews, 2011, vol. 40, pp. 696-753.

Towns, "Developments in azo disperse dyes derived from heterocyclic diazo components", Dyes and Pigments, 1999, vol. 42, pp. 3-28.

"Polymer Interface and Adhesion, Souheng Wu, Marcel Dekker, Inc., New York, 1982, p. 416".

International Search Report for PCT International Application No. PCT/US2014/071683, dated May 12, 2015, 3 pages.

Peters, "New Dyes and their Intermediates for Synthetic-polymer Fibres: III-Halogenobenzothiazolylazo Dyes", Journal of the Society of Dyers and Colourists, 1969, vol. 85, pp. 507-509.

Geng et al., "Structured Investigations on four heterocyclic disperse red azo dyes having the same benzothiazole/azo/benzene skeleton", Dyes and Pigments, 90 (2011) pp. 65-70.

* cited by examiner

DYE, FILLER MADE THEREFROM, COMPOSITIONS INCLUDING THE FILLER, AND METHOD OF DETERMINING DEGREE OF CURE OF SUCH COMPOSITIONS

CROSS-REFERENCE TO RELATED APPLICATION

This application is a national stage filing under 35 U.S.C. 371 of PCT/US2014/071683, filed Dec. 19, 2014, which claims priority to U.S. Provisional Application No. 61/921,644, filed Dec. 30, 2013, the disclosure of which is incorporated by reference in its entirety herein.

BACKGROUND

Inclusion of a dye in a curative or catalyst composition can be useful, for example, when the curative or catalyst must be admixed with a curable resin before placement and curing the resin. The dye can be useful, for example, for indicating that the curative or catalyst is uniformly mixed with the curable resin. Peroxide and dye formulations in which the color disappears when the peroxide is used to generate radicals during the cure of a curable resin are also known. See, for example, Japanese Pat. Appl. Kokai No. SHO 59-120612, published Jul. 21, 1984, and U.S. Pat. Appl. Pub. No. 2006/0202158 (Chen et al.). Although there are many ways to determine the extent of cure in cured systems, most methods require sampling and subsequent analysis of that sample using any of a number of techniques (e.g., spectroscopy, chromatography, and rheological measurements). These methods require equipment and may require interruption of a process since many of these methods cannot be performed while a manufacturing process is taking place. In addition, many of the analysis methods require a skilled user capable of interpreting results. Formulations including a dye and a catalyst or curative in which the color disappears upon curing provide a visual indication of cure, which does not require equipment or extensive interpretation.

SUMMARY

The present disclosure provides a dye compound that can be bonded onto a filler particle. The filler can then be incorporated, for example, into a composition that cures by free-radical initiated addition polymerization. The bonding of the dye compound onto the filler eliminates the potential for dye components to bloom or leech out of the cured system. Although for some compounds, modification of the dye structure can greatly alter the dye properties, we have found for the compounds disclosed herein that modification of the dye compound and bonding it to a filler can be carried out without destroying the ability of the dye to become colorless upon curing a curable composition.

In one aspect, the present disclosure provides treated filler. The treated filler includes a filler having on at least a portion of its surface a compound of formula

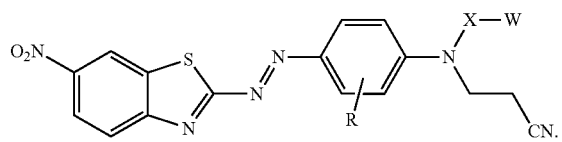

The compound is at least one of covalently bonded, ionically bonded, or hydrogen-bonded to the filler. In this compound R is hydrogen or alkyl; X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene; W is hydroxyl, a sulfonic acid group, a phosphonic acid group, carboxylic acid group, —$NHR^1$, epoxy, or —$Si(Y)_x(Z^1)_{3-x}$; $R^1$ is hydrogen, alkyl, aryl, arylalkylenyl, or alkylarylenyl; Y is alkyl, aryl, arylalkylenyl, or alkylarylenyl; each $Z^1$ is independently halide, hydroxyl, alkoxy, aryloxy, acyloxy, polyalkyleneoxy, —O— covalently bonded to the surface of the filler, or —O— bonded to another silicon atom (e.g., on another molecule of the compound) to form a siloxane, wherein alkoxy and acyloxy are optionally substituted by halogen, and wherein aryloxy is optionally substituted by halogen, alkyl, or haloalkyl; and x is 0 or 1. In some embodiments, the filler is a siliceous filler. In some of these embodiments, W is —$Si(Y)_x(Z^1)_{3-x}$, and at least one $Z^1$ is —O bonded to another silicon atom on a surface of the filler forming a siloxane bond with the surface.

In another aspect, the present disclosure provides a composition including a curable polymeric resin and the treated filler according to any of the foregoing embodiments.

In another aspect, the present disclosure provides a method for determining degree of cure of a curable polymeric resin. The method includes providing a composition comprising a curable polymeric resin, a free-radical initiator, and the treated filler in an amount sufficient to provide the composition with a first absorbance at a wavelength in a range from 400 nanometers to 700 nanometers and allowing the composition to cure to provide a cured composition, wherein the cured composition has a second absorbance at the wavelength that is different from the first absorbance.

In another aspect, the present disclosure provides a method of making a treated filler. The method includes treating a filler with a compound represented by formula:

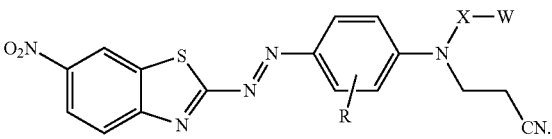

In this formula, R is hydrogen or alkyl; X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene; W is hydroxyl, a sulfonic acid group, a phosphonic acid group, carboxylic acid group, —$NHR^1$, epoxy, or —$Si(Y)_x(Z^1)_{3-x}$; $R^1$ is hydrogen, alkyl, aryl, arylalkylenyl, or alkylarylenyl; Y is alkyl, aryl, arylalkylenyl, or alkylarylenyl; $Z^1$ is halide, hydroxyl, alkoxy, aryloxy, acyloxy, polyalkyleneoxy, —O covalently bonded to a surface of the filler, or —O— bonded to another silicon atom to form a siloxane; wherein alkoxy and acyloxy are optionally substituted by halogen, and wherein aryloxy is optionally substituted by halogen, alkyl, or haloalkyl; and x is 0 or 1.

In another aspect, the present disclosure provides a compound represented by formula:

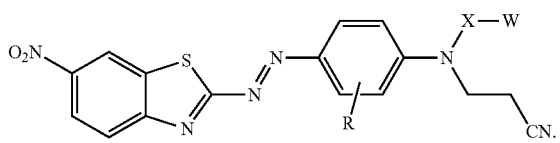

In this formula, R is hydrogen or alkyl; X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene; W is hydroxyl, a sulfonic acid group, a phosphonic acid group, carboxylic acid group, —$NHR^1$, epoxy, or —$Si(Y)_x(Z)_{3-x}$; $R^1$ is hydrogen, alkyl, aryl, arylalkylenyl, or alkylarylenyl; Y is alkyl, aryl, arylalkylenyl, or alkylarylenyl; Z is halide, hydroxyl, alkoxy, aryloxy, acyloxy, polyalkyleneoxy, or —O bonded to another silicon atom to form a siloxane, wherein alkoxy and acyloxy are optionally substituted by halogen, and wherein aryloxy is optionally substituted by halogen, alkyl, or haloalkyl; and x is 0 or 1, with the proviso that when X is ethylene, W is other than hydroxyl.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The terms "cure" and "curable" refer to joining polymer chains together by covalent chemical bonds, usually via crosslinking molecules or groups, to form a network polymer. Therefore, in this disclosure the terms "cured" and "crosslinked" may be used interchangeably. A cured or crosslinked polymer is generally characterized by insolubility, but may be swellable in the presence of an appropriate solvent.

The term "polymer or polymeric" will be understood to include polymers, copolymers (e.g., polymers formed using two or more different monomers), oligomers or monomers that can form polymers, and combinations thereof, as well as polymers, oligomers, monomers, or copolymers that can be blended.

"Alkyl group" and the prefix "alk-" are inclusive of both straight chain and branched chain groups and of cyclic groups. In some embodiments, alkyl groups have up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the multivalent (e.g., divalent or trivalent) form of the "alkyl" groups defined above.

"Arylalkylene" refers to an "alkylene" moiety to which an aryl group is attached.

"Alkylarylene" refers to an "arylene" moiety to which an alkyl group is attached.

The term "aryl" as used herein includes carbocyclic aromatic rings or ring systems, for example, having 1, 2, or 3 rings and optionally containing at least one heteroatom (e.g., O, S, or N) in the ring and optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Substituted styrene" includes alkyl, alkenyl, alkoxy, and halogen-substituted styrene.

The term "size" is considered to be equivalent with the diameter and height, for example, of glass bubbles.

All numerical ranges are inclusive of their endpoints and non-integral values between the endpoints unless otherwise stated (e.g., 1 to 5 includes 1, 1.5, 2, 2.75, 3, 3.80, 4, 5, etc.).

DETAILED DESCRIPTION

In some embodiments, the dye is represented by formula:

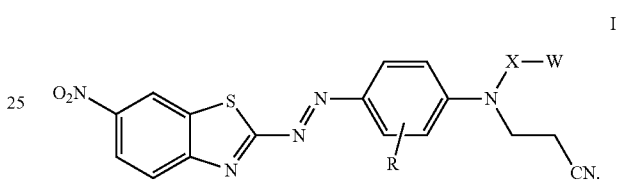

I

In formula I, R is hydrogen or alkyl. In some embodiments, R is hydrogen or alkyl having 1 to 4 carbon atoms (e.g., methyl, ethyl, n-propyl, isopropyl, n-butyl, isobutyl, or sec-butyl). In some embodiments, R is hydrogen.

In formula I, X is alkylene, arylalkylene, or alkylarylene, wherein alkylene, arylalkylene, and alkylarylene are optionally interrupted by at least one of an ether (i.e., —O—), thioether (i.e., —S—), amine (i.e., —$NR^1$—), amide (i.e., —$N(R^1)$—C(O)— or —C(O)—$N(R^1)$—), ester (i.e., —O—C(O)— or —C(O)—O—), thioester (i.e., —S—C(O)— or —C(O)—S—), carbonate (i.e., —O—C(O)—O—), thiocarbonate (i.e., —S—C(O)—O— or —O—C(O)—S—), carbamate (i.e., —$(R^1)N$—C(O)—O— or —O—C(O)—N$(R^1)$—), thiocarbamate (i.e., —$N(R^1)$—C(O)—S— or —S—C(O)—$N(R^1)$—), urea (i.e., —$(R^1)N$—C(O)—N$(R^1)$—), or thiourea (i.e., —$(R^1)N$—C(S)—N$(R^1)$—), and wherein alkylene is optionally interrupted by arylene. In any of these groups that include an $R^1$, $R^1$ is hydrogen, alkyl, aryl, arylalkylenyl, or alkylarylenyl. In some embodiments, $R^1$ is hydrogen or alkyl, for example, having 1 to 4 carbon atoms (e.g., methyl, ethyl, n-propyl, isopropyl, n-butyl, isobutyl, or sec-butyl). In some embodiments, $R^1$ is methyl or hydrogen. The phrase "interrupted by at least one functional group" refers to having part of the alkylene, arylalkylene, or alkylarylene group on either side of the functional group. An example of an alkylene interrupted by an ether is —$CH_2$—$CH_2$—O—$CH_2$—$CH_2$—. Similarly, an alkylene that is interrupted by arylene has part of the alkylene on either side of the arylene (e.g., —$CH_2$—$CH_2$—$C_6H_4$—$CH_2$—). In some embodiments, including any of the embodiments of R defined above, X is alkylene that is optionally interrupted by at least one ether, ester, carbonate, carbamate, or arylene. In some embodiments, X is alkylene that is interrupted by —O—C(O)—NH— and optionally interrupted by —O—. In these embodiments, X may be, for example, —$CH_2$—$CH_2$—O—C(O)—N(H)—$CH_2$—$CH_2$—$CH_2$—. In some embodiments, X is alkylene interrupted by —O— and arylene.

In formula I, W is hydroxyl (e.g., —OH), a sulfonic acid group (i.e., —SO$_3$M), a phosphonic acid group (i.e., —PO$_3$M), carboxylic acid group (~CO$_2$M), amino (—NHR$^1$), epoxy, or silane (—Si(Y)$_x$(Z)$_{3-x}$) or (—Si(Y)$_x$(Z$^1$)$_{3-x}$). In —NHR$^1$, R$^1$ can have any of the definitions described above. In some embodiments, including embodiments of the compound not on the surface of the filler, the treated filler, and the method of making the treated filler, W is a sulfonic acid group (i.e., —SO$_3$M), a phosphonic acid group (i.e., —PO$_3$M), carboxylic acid group (~CO$_2$M), epoxy, or silane (—Si(Y)$_x$(Z)$_{3-x}$) or (—Si(Y)$_x$(Z$^1$)$_{3-x}$). In some embodiments, W is a sulfonic acid group (i.e., —SO$_3$M), a phosphonic acid group (i.e., —PO$_3$M), carboxylic acid group (~CO$_2$M), or a silane (—Si(Y)$_x$(Z)$_{3-x}$) or (—Si(Y)$_x$(Z$^1$)$_{3-x}$). In some embodiments, W is carboxy (~CO$_2$M), or a silane (—Si(Y)$_x$(Z)$_{3-x}$) or (—Si(Y)$_x$(Z$^1$)$_{3-x}$). In some embodiments, W is a silane. In some embodiments of the compound of formula I, including embodiments of the compound not on the surface of the filler, the treated filler, and the method of making the treated filler, when X is ethylene, W is other than hydroxyl.

For any of the embodiments in which W is an acid group (e.g., a carboxylic acid, sulfonic acid, or phosphonic acid), M is hydrogen, a free anion, or a counter cation. Examples of useful counter cations include alkali metal ions (e.g., sodium, potassium, and lithium), alkaline earth metal ions (e.g., calcium and magnesium), ammonium, and alkyl ammonium (e.g., dialkylammonium, trialkylammonium, and tetraalkylammonium wherein alkyl is optionally substituted by hydroxyl, fluoride, or aryl). Compounds of formula I in which W is an acid group can be prepared as acids, in which M is hydrogen, or salts in which M is a counter cation. Free anions on the acid group are possible, for example, when the compound of formula I has an ionic interaction with the surface of a filler, as described in further detail below.

For any of the embodiments in which W is a silane (—Si(Y)$_x$(Z)$_{3-x}$) or (—Si(Y)$_x$(Z$^1$)$_{3-x}$), Y is a non-hydrolyzable group. Y is selected from the group consisting of alkyl, aryl, arylalkylenyl, and alkylarylenyl. In some embodiments, including any of the embodiments of X and R as defined above, Y is alkyl or arylalkylenyl. In some of these embodiments, Y is alkyl (e.g., methyl or ethyl).

For any of the embodiments in which W is a silane (—Si(Y)$_x$(Z)$_{3-x}$ or (—Si(Y)$_x$(Z$^1$)$_{3-x}$) each Z or Z$^1$ can independently be a halide (i.e., fluoride, chloride, bromide, or iodine), hydroxyl (i.e., —OH), alkoxy (e.g., —O-alkyl), aryloxy (e.g., —O-aryl), acyloxy (e.g., —O—C(O)-alkyl), or polyalkyleneoxy (e.g., -[EO]$_h$—[R'O]$_i$-[EO]$_h$—R" or —[R'O]$_i$-[EO]$_h$—[R'O]$_i$—R", wherein EO represents —CH$_2$CH$_2$O—; each R'O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O— (in some embodiments, —CH(CH$_3$)CH$_2$O— or —CH$_2$CH(CH$_3$)O—), each h is independently a number from 1 to 150 (in some embodiments, from 7 to about 150, 14 to about 125, 5 to 15, or 9 to 13); and each i is independently a number from 0 to 55 (in some embodiments, from about 21 to about 54, 15 to 25, 9 to about 25, or 19 to 23); and wherein R" is hydrogen or alkyl having up to four carbon atoms). Alkoxy and acyloxy are optionally substituted by halogen, and aryloxy is optionally substituted by halogen, alkyl (e.g., having up to 4 carbon atoms), or haloalkyl. In some embodiments, alkoxy and acyloxy have up to 6 (or up to 4) carbon atoms. In some embodiments, aryloxy has 6 to 12 (or 6 to 10) carbon atoms. In some embodiments, including any of the embodiments of X, R, and Y defined above, each Z or Z$^1$ is independently selected from the group consisting of halide, hydroxyl, alkoxy, aryloxy, and acyloxy. In some embodiments, each Z or Z$^1$ is independently selected from the group consisting of halide (e.g., chloride) and alkoxy having up to ten carbon atoms. In some of these embodiments, each Z or Z$^1$ is independently alkoxy having from 1 to 6 (e.g., 1 to 4) carbon atoms. In some of these embodiments, each Z or Z$^1$ is independently methoxy or ethoxy. In some embodiments, including any of the embodiments of X, R, and Y defined above, each Z or Z$^1$ is independently methoxy, acetoxy, phenoxy, bromo, or chloro. In some of these embodiments, each Z or Z$^1$ is independently methoxy, acetoxy, or chloro.

In some embodiments of the treated filler or method of making a treated filler according to the present disclosure, Z$^1$ can also be —O— covalently bonded to the surface of the filler or —O— bonded to another silicon atom to form a siloxane. For example, in a reaction medium that includes water, hydrolysis of hydrolyzable Z$^1$ groups (e.g., alkoxy, acyloxy, poly(alkyleneoxy), or halo) of reactive silanes typically generates silanol groups, which participate in condensation reactions to form siloxanes, which may be dimers, trimers, or higher oligomers from the compounds of formula I. In some embodiments, all of the hydrolysable groups may be hydrolyzed. In some of these embodiments (e.g., in the absence of filler), each Z is independently selected from the group consisting of hydroxyl and —O-covalently bonded to Si on another compound of formula I (that is, forming a siloxane bond (Si—O—Si) between two molecules of formula I.) The silanol groups typically participate in bonding interactions with silanol groups or other metal hydroxide groups on the surface of inorganic filler particles disclosed herein. The bonding interaction may be through a covalent bond (e.g., through a condensation reaction), through hydrogen bonding, or through a combination thereof. It is reported in *Polymer Interface and Adhesion*, Souheng Wu, Marcel Dekker, Inc., New York, 1982, p. 416, that hydrogen bonding of the silanol groups to a glass surface usually occurs first, and then condensation reactions between silanol groups of adjacent silane molecules can form a polysiloxane monolayer on the glass surface. Hydrogen bonded silanols and condensed polysiloxanes also occurs in the upper layers, and the silanes surrounding the particles may be hydrogen bonded or covalently bonded. This phenomenon also occurs with other materials that bear hydroxyl groups on the surface (that is, other than glass). Accordingly, in some embodiments, particularly of treated filler or methods of making a treated filler, each Z or Z$^1$ is independently selected from the group consisting of hydroxyl, alkoxy, —O— covalently bonded to the surface of the filler, and —O— covalently bonded to Si on another compound of formula I (that is, forming a siloxane bond (Si—O—Si) between two molecules of formula I).

For any of the embodiments in which W is a silane (—Si(Y)$_x$(Z)—$_{3-x}$) or (—Si(Y)$_x$(Z$^1$)$_{3-x}$), x is 0 or 1. Typically x is 0.

Compounds of formulas I can be prepared, for example, beginning with an ester represented by formula X

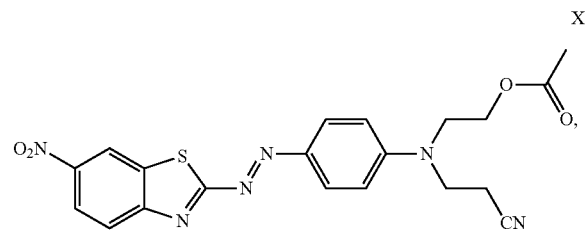 [SMILES: CC(=O)OCCN(CCC#N)c1ccc(/N=N/c2nc3ccc([N+](=O)[O-])cc3s2)cc1]

which is commercially available, for example, from Winchem Industrial Co. Ltd, China, and China Langchem Inc., China as "DISPERSE RED 177". This compound can be hydrolyzed under known saponification conditions to provide the hydroxyl compound, an example of a compound shown below in formula XI. Alternatively, compounds of formula I can be prepared by treating commercially available 2-amino-6-nitrobenzothiazole with nitrosyl sulfuric acid solution prepared in situ from sodium nitrite in concentrated sulfuric acid according to the method described in Chen, L. et al. *Dyes and Pigments*, 2007, vol. 73, pages 338 to 343. The reaction can conveniently be carried out in a mixture of dichloroacetic acid and glacial acetic acid or a mixture of phosphoric acid and acetic acid after cooling below room temperature. The resultant diazonium sulfate salt can be coupled with N-(2-cyanoethyl)-N-(2-hydroxyethyl)aniline. Other N-(2-cyanoethyl)-N-(2-hydroxyalkyl)-anilines, which can be prepared by known methods, can also be useful in the coupling reaction.

The resultant compounds of formula XI:

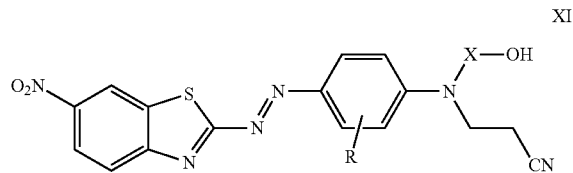

can be converted to compounds according to formula I using a variety of known synthetic methods. For example, compounds of formula XI can be treated with isocyanatoalkyl silanes to provide compounds of formula I in which X is alkylene interrupted by a —O—C(O)—NR$^1$— and W is —Si(Y)$_x$(Z)$_{3-x}$. Such reactions can be carried out in the presence of tin compounds (e.g., dibutyltin dilaurate) at ambient temperature although the reaction can also be carried out in the absence of a catalyst or promoter. Isocyanato alkylene esters are also useful to provide a compound of formula I in which X is alkylene interrupted by a —O—C(O)—NR$^1$— and W is a carboxylic acid group. Some of these isocyanatoalkylene esters (e.g., ethyl 3-isocyanatopropionate) are commercially available. Others may be prepared by conventional methods. Hydrolysis of the ester using conventional methods can provide a compound in which W is a carboxylic acid group.

Compounds of formula XI can also react with carboxylic acids and phenols under Mitsunobu reaction conditions. Typically the Mitsunobu coupling is carried out in the presence of triphenyl phosphine and diisopropyl azodicarboxylate or diethyl azodicarboxylate in a suitable solvent. The reaction can conveniently be carried out at or below ambient temperature. Under these conditions compounds of formula XI can be reacted, for example, with 5-sulfopentaoic acid, sulfoacetic acid, or a salt or ester of the sulfonic acid group of these to provide a compound in which X is alkylene interrupted by —O—C(O)—, and W is a sulfonic acid group. When an ester of the sulfonic acid is used, exclusion of water from the reaction mixture may be beneficial, and the product sulfonic acid ester can be hydrolyzed after the coupling reaction using conventional methods. The Mitsunobu coupling reaction can also be carried out with phenols. For example, compounds of formula XI can be treated with methyl 3-(4-hydroxyphenyl)propionate or methyl 4-hydroxyphenylacetate followed by hydrolysis of the ester to provide a compound of formula I in which X is alkylene interrupted by —O— and arylene, and W is a carboxylic acid group. Reaction of a compound of formula XI with hydroquinone may also be useful. After purification of the statistical mixture of reaction products of the compound of formula XI and hydroquinone, a compound of formula I in which X is —CH$_2$CH$_2$—O—C$_6$H$_4$—, and W is OH can be treated with epichlorohydrin under basic conditions to provide a compound in which X is —CH$_2$CH$_2$—O—C$_6$H$_4$—OCH$_2$—, and W is an epoxy group.

The hydroxyl group in the compound of formula XI can also be converted to an amine or thiol using standard functional group manipulation. The resultant amines or mercaptans can be reacted with isocyanatoalkyl silanes as described above, haloalkyl silanes, or with acrylate functional alkylsilanes to provide X groups in which alkylene is interrupted by thioether (i.e., —S—), amine (i.e., —NR$^1$—), urea (i.e., —(R$^1$)N—C(O)—N(R$^1$)—), and/or ester (—C(O)—O—), and W is (—Si(Y)$_x$(Z)$_{3-x}$) in the compounds of formula I. The resultant amines or mercaptans can also be reacted with alpha, beta-unsaturated carboxylic acids, phosphonic acids, and sulfonic acids to provide compounds in which W is sulfonic acid group, phosphonic acid group, or a carboxylic acid group, and X is alkylene interrupted by amine or thioether.

The hydroxyl group in the compound of XI can also be converted to a good leaving group (e.g., mesylate or tosylate) and treated with amino-functional silanes or amino-functional acids or their salts or esters. For example, the mesylate of the compound of formula XI can react with 2-aminoethylsulfonic acid, aminomethyl phosphonic acid, 2-aminoethyl phosphonic acid, 3-aminopropyl phosphonic acid, or salts (e.g., sodium salt) or esters of any of these acids to provide a compound in which X is alkylene interrupted with —N(H)—, and W is a sulfonic acid group, phosphonic acid group, or an ester thereof. The mesylate or tosylate of the compound of formula XI can react with diamines to provide a compound of formula XI in which W is an amino group. For example, an alkylene diamine can be reacted with the mesylate of the compound of formula XI, and the resulting mixture can be purified to provide a compound in which X is alkylene interrupted with —N(R$^1$)—, and W is —NHR$^1$. Alternatively, one amino group can be protected before the reaction of the diamine with the mesylate of the compound of formula XI, and the resultant product can be deprotected to provide the compound in which W is —N(R$^1$)—. Phosphite esters can also be useful nucleophiles to displace the activated hydroxyl group and provide, after hydrolysis of the ester groups, compounds of formula I in which X is alkylene and W is a phosphonic acid group.

The compounds of formulas I are useful, for example, for treating fillers, generally inorganic fillers. The fillers can be microfillers, nanofillers, macrofillers, or fibrous fillers. The fillers can be made, for example, of alumina, tin oxides, antimony oxides, silica, zirconia, titania, mixed oxides of any of these, glass, ceramics, a mineral such as mica, woolastonite, talc, clay, and combinations of any of these fillers. The term "ceramic" refers to glasses, crystalline ceramics, glass-ceramics, and combinations thereof. Alumina, tin oxides, antimony oxides, silica, zirconia, titania, mixed oxides of any of these, and the minerals can be of any desired size, including particles having an average size above 1 micrometer, between 100 nanometers (nm) and 1 micrometer, and below 100 nm. In the treated fillers according to the present disclosure, the compound of formula I can be attached to the filler covalently, ionically or through strong physisorption.

In some embodiments, the compounds of formulas I are useful, for example, for treating siliceous fillers. In these embodiments, typically W in formula I is a silane (—Si(Y)$_x$(Z)$_{3-x}$) or (—Si(Y)$_x$(Z$^1$)$_{3-x}$), in which Y, Z, Z$^1$, and x are as defined in any of their embodiments described above. The siliceous filler may be silica of any desired size, including particles having an average size above 1 micrometer, between 100 nm and 1 micrometer, and below 100 nm.

Silica can include nanosilica and amorphous fumed silica, for example. In some embodiments, the siliceous filler comprises silica nanoparticles having a particle size of greater than 1 nm and up to 100 nm. Silica nanoparticles can have a particle size from 5 nm to 75 nm or 10 nm to 30 nm or 20 nm. Examples of commercially available nanosilica suitable for treatment with a compound of formula I include those available from Nalco Chemical Co. (Naperville, Ill.) under the trade designation "NALCO COLLOIDAL SILICAS". For example, silicas include NALCO products 1040, 1042, 1050, 1060, 2327 and 2329. Suitable fumed silicas include for example, products available from DeGussa AG, (Hanau, Germany) under the trade designation "AEROSIL", for example, series OX-50, -130, -150, and -200, and from Cabot Corp. (Tuscola, Ill.) under the trade designations "CAB-O-SPERSE 2095", "CAB-O-SPERSE A10 5", and "CAB-O-SIL M5".

In some embodiments, the siliceous filler comprises hollow glass elements, such as hollow spheres (e.g., microspheres) and spheroids. Examples of commercially available materials suitable for use as the hollow, glass elements include glass bubbles marketed by 3M Company, Saint Paul, Minn., as "3M GLASS BUBBLES" in grades K1, K15, K20, K25, K37, K46, S15, S22, S32, S35, S38, S38HS, S38XHS, S42HS, S42XHS, S60, S60HS, iM30K, iM16K, XLD3000, XLD6000, and G-65, and any of the HGS series of "3M GLASS BUBBLES"; glass bubbles marketed by Potters Industries, Carlstadt, N.J., under the trade designations "Q-CEL HOLLOW SPHERES" (e.g., grades 30, 6014, 6019, 6028, 6036, 6042, 6048, 5019, 5023, and 5028); and hollow glass particles marketed by Silbrico Corp., Hodgkins, Ill. under the trade designation "SIL-CELL" (e.g., grades SIL 35/34, SIL-32, SIL-42, and SIL-43). Solid glass spheres are also useful as treated fillers according to the present disclosure, for example, solid glass spheres available from Cospheric LLC, Santa Barbara, Calif. as "SODA LIME SOLID GLASS MICROSPHERES", "BOROSILICATE SOLID GLASS MICROSPHERES", "BARIUM TITANATE GLASS SPHERES", and "E GLASS SPHERES".

In some embodiments, the siliceous filler comprises hollow, ceramic elements made from ceramics such as alumina silicates. In some embodiments, the discrete, hollow, ceramic elements are aluminosilicate microspheres extracted from pulverized fuel ash collected from coal-fired power stations (i.e., cenospheres). Useful cenospheres include those marketed by Sphere One, Inc., Chattanooga, Tenn., under the trade designation "EXTENDOSPHERES HOLLOW SPHERES" (e.g., grades SG, MG, CG, TG, HA, SLG, SL-150, 300/600, 350 and FM-1). Other useful hollow, ceramic spheroids include silica-alumina ceramic hollow spheres with thick walls marketed by Valentine Chemicals of Lockport, La., as ZEEOSPHERES CERAMIC MICROSPHERES in grades N-200, N-200PC, N-400, N-600, N-800, N1000, and N1200. Solid ceramic spheres are also useful as treated fillers according to the present disclosure, for example, ceramic microspheres marketed by 3M Company under the trade designation "3M CERAMIC MICROSPHERES" (e.g., grades W-610 and W-410).

The hollow glass or ceramic elements may have one of a variety of useful sizes but typically has a maximum dimension of less than 10 millimeters (mm), more typically less than one mm. In some embodiments, the hollow glass elements have a maximum dimension in a range from 0.1 micrometer to one mm, from one micrometer to 500 micrometers, from one micrometer to 300 micrometers, or even from one micrometer to 100 micrometers. The mean particle size of the hollow, glass elements may be, for example, in a range from 5 to 250 micrometers (in some embodiments from 10 to 110 micrometers, from 10 to 70 micrometers, or even from 20 to 50 micrometers).

In some embodiments, the siliceous filler is a macrofiller prepared, for example, by grinding or crushing quartz, glass, borosilicate, or ceramics to a desired size range (e.g., in a range from 0.8 micrometers to 2 micrometers. The siliceous filler may also be glass or ceramic fibers. Such fibers may have, for example, diameters in a range from 2 micrometers to 50 micrometers, in some embodiments 5 micrometers to 25 micrometers and lengths of at least about 500 micrometers. In some embodiments, fibers from an essentially continuous mat, which may have undetermined length, are useful. In some embodiments, the fibers have a length in a range from 1/16 inch (1.6 mm) to 1.5 inches (38.1 mm) long. In some embodiments, the fibers have a length in a range from 1/16 inch (1.6 mm) to about 0.5 inch (12.7 mm). In other embodiments, the fibers have a length in a range from one inch (25.4 mm) to 1.5 inches (38.1 mm).

It is typically useful to treat the siliceous filler with a compound of formula I in which W is a silane such that approximately a monolayer of the dye is attached to the surface of a filler particle. For example, in embodiments in which the siliceous filler includes glass bubbles, in general, one equivalent of the compound of formula I should be used per hydroxyl group on the glass bubbles. Using this stoichiometry, multiple layers of siloxane on the surface of the glass bubbles, which may lead to inaccessibility of some of the dye in a free-radical reaction, described further below, can be avoided.

In some embodiments, the compounds of formulas I are useful, for example, for treating zirconia. In some of these embodiments, the inorganic filler treated with a compound of formula I comprises zirconia nanoparticles. Zirconia nanoparticles can have a particle size from 5 nm to 50 nm, 5 nm to 15 nm, or about 10 nm. Zirconias suitable for treatment with a compound of formula I are commercially available, for example, from Nalco Chemical Co. under the trade designation "NALCO OOSSOO8". In some embodiments, the inorganic filler treatment with a compound of formula I comprises zirconia hollow ceramic microspheres.

In some embodiments, the compounds of formulas I are useful, for example, for treating titania, antimony oxides, alumina, tin oxides, and/or mixed metal oxide fillers. Such fillers can have a variety of useful sizes as described above. In some embodiments, the titania, antimony oxides, alumina, tin oxides, and/or mixed metal oxide fillers comprise nanoparticles having a particle size or associated particle size from 5 nm to 50 nm, or 5 nm to 15 nm, or about 10 nm. Mixed metal oxides suitable for treatment with a compound of formula I are commercially available, for example, from Catalysts & Chemical Industries Corp., (Kawasaki, Japan) under the product designation "OPTOLAKE 3".

Inorganic fillers may be treated with compounds of formulas I using a variety of methods. The type of treatment agent of formula I and method are determined, in part, by the chemical nature of the filler surface. As described above, compounds of formulas I in which W is a silane are useful for treating siliceous fillers. Compounds of formulas I in which W is a silane or an acid group (e.g., carboxylic acid, sulfonic acid, or phosphonic acid) may be useful, for example, for treating zirconia and minerals such as mica, woolastonite, talc, and clay. The required amount of the compound of formula I is dependent upon several factors including particle size, particle type, and the particular compound of formula I. In general it is useful for approximately a monolayer of the compound of formula I to be attached to the surface of the particle. The attachment procedure or reaction conditions required also depend on the particular compound of formula I used. When W is a carboxylic acid, elevated temperature or extended time may not be necessary.

For treating siliceous filler (e.g., hollow glass or ceramic elements), zirconia, or a mineral such as mica, woolastonite, talc, clay with the compound of formula I, in which W is a silane, a useful method typically includes combining the compound of formula I with the siliceous filler in a medium comprising water. Hydrolysis of the Z groups in a compound of formula I typically generates silanol groups, which participate in condensation reactions to form siloxanes and/or participate in bonding interactions with silanol groups on siliceous fillers. Hydrolysis can occur, for example, in the presence of water optionally in the presence of an acid or base. The water necessary for hydrolysis is typically added to a composition containing the compound of formula I and the siliceous filler, although, in some cases, the water may be adsorbed to the surface of the filler, or may be present in the atmosphere to which the filler is exposed (e.g., an atmosphere having a relative humidity of at least 10%, 20%, 30%, 40%, or even at least 50%). The rate of the condensation reaction is typically dependent upon temperature, pH, and the concentration of the compound of formula I. In some embodiments, it is useful to surface treat filler with a compound or formula I in which W is a silane at elevated temperatures under acidic or basic conditions for approximately one to 24 hours. The surface modification of zirconia with a compound of formula I in which W is a silane can be carried out by heating under acid conditions for a suitable period of time after which the dispersion is combined with aqueous ammonia (or other base). This method allows removal of the acid counter ion from the zirconia surface as well as reaction with the silane. The particles may then be separated from the liquid phase.

The surface modification of the particles in the colloidal dispersion (e.g., nanoparticles) can be accomplished in a variety of ways. For example, mixing an inorganic dispersion with a compound of formula I optionally in a co-solvent (e.g., 1-methoxy-2-propanol, ethanol, isopropanol, ethylene glycol, N,N-dimethylacetamide and N-methyl-2-pyrrolidinone) can be useful. The co-solvent can enhance the solubility of the compound of formula I as well as the treated particles. The mixture comprising the inorganic sol and compound of formula I is subsequently reacted at room temperature or an elevated temperature, with or without mixing. Conveniently, the mixture can be reacted at about 85° C. for about 24 hours, resulting in the surface modified sol. When metal oxides are treated with a compound of formula I, the surface treatment of the metal oxide can involve the adsorption of acidic molecules (e.g., compounds in which W is a sulfonic acid group, a phosphoric acid group, or carboxylic acid group) to the particle surface, which can take place, for example, at room temperature.

In some embodiments, an inorganic filler can be treated with a compound of formula I using a two-step process in which first the inorganic filler is treated with a surface treatment agent, and the resulting functionalized filler is treated with a compound of formula I. For example, using any of the methods described above a siliceous filler or zirconia as described in any of the aforementioned embodiments may be treated with 3-(methacryloyloxy)propyltrimethoxysilane, 3-acryloxypropyltrimethoxysilane, 3-(methacryloyloxy)propyltriethoxysilane, 3-(methacryloyloxy) propylmethyldimethoxysilane, 3-(acryloyloxypropyl) methyldimethoxysilane, 3-(methacryloyloxy)propyldimethylethoxysilane, 3-(methacryloyloxy) propyldimethylethoxysilane, 3-glycidoxypropyltrimethoxysilane, acrylic acid, methacrylic acid, or beta-carboxyethylacrylate. The resulting acrylate-, methacrylate-, or epoxyfunctional filler can then be treated with a compound of formula I in which W is a hydroxyl or amino group using conventional methods.

Treated fillers according to the present disclosure can be useful in compositions including a curable polymeric resin, for example. The curable polymeric resins are curable by free-radical polymerization. Examples of suitable curable polymeric resin include acrylics, epoxies, urethanes, silicones, vinyl esters, polyesters, ene-thiol compositions, and combinations thereof. As would be understood by a person of ordinary skill in the art, a vinyl ester is a resin produced by the esterification of an epoxy resin with an unsaturated monocarboxylic acid.

Ene-thiol compositions, which are also referred to as thiol-ene compositions, are those compositions comprising a polythiol and at least one unsaturated compound comprising two or more carbon-carbon double bonds, carbon-carbon triple bonds, or a combination thereof. Suitable unsaturated compounds include dienes, diynes, divinyl ethers, diallyl ethers, ene-ynes, and trifunctional versions of any of these. Combinations of any of these groups may also be useful. A polythiol is a compound having at least two mercaptan groups (e.g., 2, 3, or 4 mercaptan groups). Polythiols include monomeric compounds and oligomeric compounds. A monomeric polythiol may be an alkylene, arylene, alkylarylene, arylalkylene, or alkylenearylalkylene having at least two mercaptan groups, wherein any of the alkylene, alkylarylene, arylalkylene, or alkylenearylalkylene are optionally interrupted by one or more ether (i.e., —O—), thioether (i.e., —S—), or amine (i.e., —NR$^1$—) groups and optionally substituted by alkoxy or hydroxyl. A useful oligomeric or polymeric polythiol may be a polythioether made, for example, by reacting dithiols with dienes, diynes, divinyl ethers, diallyl ethers, ene-ynes, or combinations of these under free-radical conditions, by reacting dithiols with diepoxides, or by a combination of such methods. See, for example, polythioethers in U.S. Pat. No. 4,366,307 (Singh et al.), U.S. Pat. No. 4,609,762 (Morris et al.), U.S. Pat. No. 5,225,472 (Cameron et al.), U.S. Pat. No. 5,912,319 (Zook et al.), U.S. Pat. No. 5,959,071 (DeMoss et al.), U.S. Pat. No. 6,172,179 (Zook et al.), and U.S. Pat. No. 6,509,418 (Zook et al.). A useful oligomeric or polymeric polythiol may also be a polysulfide prepared, for example, by the condensation of sodium polysulfide with bis-(2-chloroethyl) formal. See, for example, in U.S. Pat. No. 2,466,963 (Patrick et al); U.S. Pat. No. 2,789,958 (Fettes et al); U.S. Pat. No. 4,165,425 (Bertozzi); and U.S. Pat. No. 5,610,243 (Vietti et al.). Ene-thiol compositions cure by free-radical initiated polymerization, for example, in the presence of a free-radical initiator.

The curable polymeric resin can include one or more non-reactive polymeric materials, as desired, for a particular application. Compositions including a curable polymeric resin and a filler according to the present disclosure may be combined with a free-radical initiator to cure the composition as described in further detail below. Treated fillers according to the present disclosure can be included in compositions including a curable polymeric resin in an amount of at least 1, 5, 10, 20, 30, 40, or 50 percent by weight up to about 75 percent by weight, based on the total weight of the composition. Mixtures of more than one type treated filler may be used together in the curable polymeric resins.

For many embodiments of the treated fillers according to the present disclosure, the fillers can be mixed in a curable polymeric resin using conventional mixing. When the treated fillers are prepared from a colloidal dispersion (e.g., nanoparticles) a variety of methods for incorporating the treated fillers into a curable polymeric resin may be useful. For example, a solvent exchange procedure may be useful. In a solvent exchange method, the curable polymeric resin can be added to the surface modified sol, followed by removal of the water and co-solvent (if used) via evaporation, thus leaving the particles dispersed in the curable polymeric resin. The evaporation step can be accomplished, for example, via distillation, rotary evaporation, or oven drying. In another example, the surface modified particles can be extracted into a water immiscible solvent followed by solvent exchange. Another method involves the drying of the modified particles into a powder, followed by the addition of the curable polymeric resin into which the particles are dispersed. Drying can be carried out using a variety of suitable methods (e.g., oven drying or spray drying).

One application of compositions according to the present disclosure that include curable polymeric resins are curable body repair materials useful in the repair of damaged vehicles and other equipment (e.g., cars, trucks, watercraft, windmill blades, aircraft, recreational vehicles, bathtubs, storage containers, and pipelines). Curable body repair materials can include two reactive components (e.g., a curable polymeric resin and catalyst or initiator) which are mixed together to form the curable body repair material. The volumetric ratio of the reactive components may be in the range of, e.g., 1:1 or higher (where higher is, e.g., 2:1, 3:1, etc.) for epoxy or urethane compounds and may be 20:1 or higher, or 25:1 or higher, or 30:1 or higher for unsaturated polyesters with a peroxide catalyst as an initiator. The curable body repair materials may include additives to enhance adhesion of the curable body material to common repair surfaces (e.g., aluminum, galvanized steel, E-coats, primers, and paints). The adhesion promoting additives may have, for example, anhydride functionality, silane functionality, or amine functionality and may or may not be covalently incorporated into the base resin.

In some embodiments, the curable polymeric resin is an unsaturated polyester resin. Unsaturated polyester resins include a polyester generally formed by a polycondensation reaction of an unsaturated dicarboxylic acid (e.g., maleic acid or fumaric acid) with a dihydroxy compound (e.g., a glycol) or diamine. Saturated dicarboxylic acids or equivalents (e.g., phthalic anhydride) can also be included. In some embodiments, the curable polymeric resin further includes at least one of styrene monomer, a substituted styrene monomer (e.g., alpha-methyl styrene, p-methyl styrene, or divinylbenzene), an acrylate monomer, a methacrylate monomer, or any compound that can be copolymerized with the unsaturated polyester resin. Illustrative curable, unsaturated polyester based compositions are described in U.S. Pat. No. 6,063,864 (Mathur et al.); U.S. Pat. No. 5,456,947 (Parish et al.); U.S. Pat. No. 4,980,414 (Naton); U.S. Pat. No. 5,028,456 (Naton); and U.S. Pat. No. 5,373,036 (Parish et al.).

Other illustrative curable, unsaturated polyester based compositions are described in Int. Pat. Appl. Pub. No. WO 95/19379 (Ruggeberg).

Body filler compositions may include other filler in addition to the treated filler according to the present disclosure. In some embodiments, the composition according to the present disclosure further includes at least one of polymer beads, hollow polymeric elements, sodium metaborate, polymer fibers, carbon or metal fibers, dolomite, or calcium carbonate. In some embodiments, the composition according to the present disclosure also includes any one of the fillers described above (e.g., alumina, tin oxides, antimony oxides, silica, zirconia, titania, mixed oxides of any of these, minerals (e.g., mica, woolastonite, talc, and clay), glass, ceramics, and combinations thereof) that is not treated. In some embodiments, it may be useful for the filler in the composition including a curable polymeric resin to be limited to the treated filler according to the present disclosure. This may be useful, for example, to help visualize a color change in the composition as described in further detail, below.

Compositions according to the present disclosure including a curable polymeric resin and a treated filler disclosed herein can further include a free-radical initiator. Any free-radical initiator may be useful. In some embodiments, the free-radical initiator is an organic peroxide. Examples of useful organic peroxides include hydroperoxides (e.g., cumene, tert-butyl or tert-amyl hydroperoxide), dialkyl peroxides (e.g., di-tert-butyl, dicumylperoxide, or cyclohexyl peroxide), peroxyesters (e.g., tert-butyl perbenzoate, tert-butyl peroxy-2-ethylhexanoate, tert-butyl peroxy-3,5,5-trimethylhexanoate, tert-butyl monoperoxymaleate, or di-tert-butyl peroxyphthalate), peroxycarbonates (e.g., tert-butylperoxy 2-ethylhexylcarbonate, tert-butylperoxy isopropyl carbonate, or di(4-tert-butylcyclohexyl) peroxydicarbonate), ketone peroxides (e.g., methyl ethyl ketone peroxide, 1,1-di(tert-butylperoxy)cyclohexane, 1,1-di(tert-butylperoxy)-3,3,5-trimethylcyclohexane, and cyclohexanone peroxide), and diacylperoxides (e.g., benzoyl peroxide or lauryl peroxide). The organic peroxide may be selected, for example, based on the temperature desired for use of the organic peroxide and compatibility with a curable polymeric resin desired to be cured. Combinations of two or more organic peroxides may also be useful.

The free-radical initiator may also be a photoinitiator. Examples of useful photoinitiators include benzoin ethers (e.g., benzoin methyl ether or benzoin butyl ether); acetophenone derivatives (e.g., 2,2-dimethoxy-2-phenylacetophenone or 2,2-diethoxyacetophenone); 1-hydroxycyclohexyl phenyl ketone; and acylphosphine oxide derivatives and acylphosphonate derivatives (e.g., bis(2,4,6-trimethylbenzoyl)phenylphosphine oxide, diphenyl-2,4,6-trimethylbenzoylphosphine oxide, isopropoxyphenyl-2,4,6-trimethylbenzoylphosphine oxide, or dimethyl pivaloylphosphonate). Many photoinitiators are available, for example, from BASF (Florham Park, N.J.), under the trade designation "IRGACURE". The photoinitiator may be selected, for example, based on the desired wavelength for curing and compatibility with a curable polymeric resin desired to be cured.

For convenience, compositions according to the present disclosure including a curable polymeric resin and a treated filler disclosed herein can be combined with a formulation including the free-radical initator and a diluent. The diluent can be a plasticizer, mineral spirits, water, or a solvent such as N-methyl-2-pyrrolidone, tetrahydrofuran, or ethyl acetate. Some pastes including a diluent and a peroxide such as benzoyl peroxide, ketone peroxides (e.g., methyl ethyl ketone peroxide), hydroperoxides (e.g., cumene hydroperoxide), peroxyesters (e.g., t-butyl peroxy-2-ethylhexanoate), and diperoxyketals are sold commercially.

For repairing an automobile, for example, a technician typically mixes the two reactive components and then uses a squeegee to spread the repair compound onto the surface of the vehicle to roughly match the contour of the surface. As the curable polymeric resin reacts with the curative or initiator, it hardens to a state where it can be shaped to match the contour of the vehicle before it was damaged. During this hardening process, the body filler typically transitions from a state of soft, gelled material to a state of moderately hard material that is relatively easy to shape with an abrasive article (e.g., sandpaper) to a state of hard material. In some embodiments, the body filler is a filled unsaturated polyester resin that is mixed with a peroxide to facilitate crosslinking at room temperature.

The process of repairing dents using body filler can present challenges. Body filler typically requires handling in a relatively narrow time window. Premature sanding of body filler before it has reached a critical amount of cure results in sandpaper becoming plugged thereby reducing its effectiveness, the surface of the body filler becoming rough, and sometimes the body filler peeling away from the surface of the vehicle. If this situation occurs, then typically the body filler has to be partially removed (usually by sanding) such that another layer of body filler can be put on top and properly shaped. Waiting too long before shaping the body filler can lengthen the time required to repair the dent as the body filler becomes hardened to a point where the material can be difficult to shape. Most body filler systems are now formulated to cure to a good shaping state in a relatively short amount of time (e.g., 4 to 12 minutes). Identifying the time period when the body filler has transitioned into the state where it is relatively easy to shape is important to speed up that part of the repair process.

Other processes that may be enhanced by recognizing the extent of cure in a curable composition include curing medical adhesives and dental composites or adhesives. In some of these applications, the curable composition includes a photoinitiator. In some embodiments, these compositions include acrylate, methacrylate, acrylamide, or methacrylamide monomers in combination with oligomeric urethane acrylates or methacrylate or other functional oligomers.

In some embodiments, compositions according to the present disclosure including an ene-thiol curable composition and a treated filler disclosed herein can be useful as sealants, for example, aviation fuel resistant sealants. Aviation fuel resistant sealants are widely used by the aircraft industry for many purposes. Principal among these uses are the sealing of integral fuel tanks and cavities, the sealing of the passenger cabin to maintain pressurization at high altitude, and for the aerodynamic smoothing of the aircraft's outer surfaces. In some of these applications, the curable composition includes a photoinitiator.

In compositions that are light cured, the compositions according to the present disclosure also provide the advantage that they can indicate when they have been exposed to a curing light. In these cases, the disappearance or muting of the color can indicate that the compositions have been exposed to the curing light. The color change in the presently disclosed compositions indicates that free radicals have been generated, which may distinguish these compositions from those that undergo photobleaching. This feature can be beneficial when a manufacturing line has been stopped, for example, so that operators can easily differentiate exposed and unexposed compositions.

In some embodiments, compositions according to the present disclosure include a treated filler disclosed herein and one or more monomers (e.g., styrene, a substituted styrene, acrylate, methacrylate, acrylamide, or methacrylamide monomers). In some of these embodiments, the composition further includes a free-radical initiator.

The fillers treated with a compound of formula I according to the present disclosure can be useful for indicating curing in the applications described above. The compounds of formulas I change color in the presence of free-radicals, and thus can directly indicate cure by correlation of the concentration of free-radicals in the system. Fillers treated with compounds of formulas I have an initial colored state and a less colored or colorless final state, as demonstrated in the examples, below. For many applications, such as auto repair or dental applications, a colorless or nearly colorless final state is highly desirable. In auto repair, a cure indicator that retains a specific color in its cured state can be problematic when it comes to painting. Furthermore, since the compound of formula I is bonded to the filler, it advantageously does not migrate out of the cured system over time.

Accordingly, the present disclosure also provides a method for determining degree of cure of a curable polymeric resin, including any of the curable polymeric resins described above. The method includes providing a composition comprising a curable polymeric resin, a free-radical initiator, and a treated filler according to the present disclosure in an amount sufficient to provide the composition with a first absorbance at a wavelength in a range from 400 nanometers to 700 nanometers. The wavelength may be in a range, for example, from 450 nanometers to 650 nanometers, typically in a range from 500 nanometers to 550 nanometers. Allowing the composition to cure or curing the composition provides a cured composition that has a second absorbance at the wavelength that is different from the first absorbance. In some embodiments, the absorbance at the selected wavelength is decreased by at least 20, 25, 30, 35, 40, 45, or 50 percent or more. The initial and final absorbance can be measured, for example, using a UV/VIS spectrometer or a colorimeter. A composition having an absorbance at a wavelength in a range from 400 nanometers to 700 nanometers would typically be perceived by the human eye as a particular color. In some embodiments, a color in the composition is no longer visible in the cured composition. In these embodiments, a difference between the second absorbance and the first absorbance is visually determined. In some embodiments, providing the composition includes mixing the curable polymeric resin including the treated filler with a curative comprising the free-radical initiator. The free-radical initiator may be any of those described above, and the curative may also include any of the diluents described above. Advantageously, mixing can be carried out until the visible color of the treated filler is uniformly dispersed in the composition.

Some Embodiments of the Disclosure

In a first embodiment, the present disclosure provides a compound represented by formula:

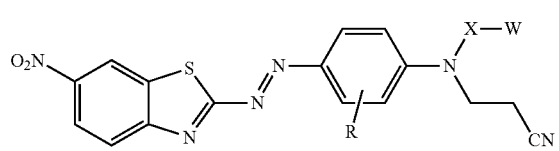

R is hydrogen or alkyl;

X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is hydroxyl, a sulfonic acid group, a phosphonic acid group, a carboxylic acid group, —NHR$^1$, epoxy, or —Si(Y)$_x$(Z)$_{3-x}$;

R$^1$ is hydrogen, alkyl, aryl, arylalkylenyl, or alkylarylenyl;

Y is alkyl, aryl, arylalkylenyl, or alkylarylenyl;

each Z is independently halide, hydroxyl, alkoxy, aryloxy, acyloxy, polyalkyleneoxy, or —O bonded to another silicon atom to form a siloxane, wherein alkoxy and acyloxy are optionally substituted by halogen, and wherein aryloxy is optionally substituted by halogen, alkyl, or haloalkyl; and x is 0 or 1, with the proviso that when X is ethylene, W is other than hydroxyl.

In a second embodiment, the present disclosure the compound of the first embodiment, represented by formula:

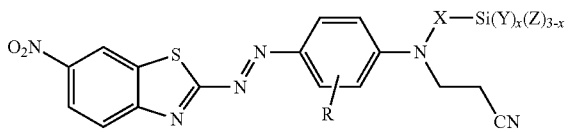

wherein

R is hydrogen or alkyl;

X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

Y is alkyl, aryl, arylalkylenyl, or alkylarylenyl;

each Z is independently halide, hydroxyl, alkoxy, aryloxy, acyloxy, polyalkyleneoxy, or —O bonded to another silicon atom to form a siloxane, wherein alkoxy and acyloxy are optionally substituted by halogen, and wherein aryloxy is optionally substituted by halogen, alkyl, or haloalkyl; and x is 0 or 1.

In a third embodiment, the present disclosure provides the compound of the first or second embodiment, wherein R is hydrogen.

In a fourth embodiment, the present disclosure provides the compound of the first embodiment, wherein W is —Si(Y)$_x$(Z)$_{3-x}$.

In a fifth embodiment, the present disclosure provides the compound of any one of the first to fourth embodiments, wherein x is 0, and wherein Z is alkoxy.

In a sixth embodiment, the present disclosure provides the compound of any one of the first to fifth embodiments, wherein X is alkylene that is optionally interrupted by at least one ether, ester, carbonate, carbamate, or arylene.

In a seventh embodiment, the present disclosure provides the compound of any one of the first to sixth embodiments, wherein X is alkylene that is interrupted by —O—C(O)—NH— and optionally interrupted by —O—.

In an eighth embodiment, the present disclosure provides a treated filler comprising the compound of any one of first to seventh embodiments at least one of covalently bonded, ionically bonded, or hydrogen-bonded to a filler.

In a ninth embodiment, the present disclosure provides treated filler comprising:

a filler having on at least a portion of its surface a compound of formula

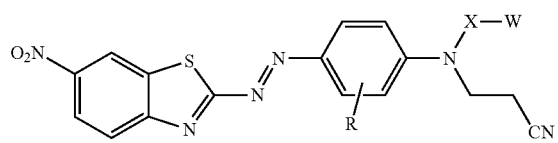

wherein

R is hydrogen or alkyl;

X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is hydroxyl, a sulfonic acid group, a phosphonic acid group, carboxylic acid group, —NHR$^1$, epoxy, or —Si(Y)$_x$(Z$^1$)$_{3-x}$;

R$^1$ is hydrogen, alkyl, aryl, arylalkylenyl, or alkylarylenyl;

Y is alkyl, aryl, arylalkylenyl, or alkylarylenyl;

each Z$^1$ is independently halide, hydroxyl, alkoxy, aryloxy, acyloxy, polyalkyleneoxy, —O— covalently bonded to the surface of the filler, or —O— bonded to another silicon atom to form a siloxane, wherein alkoxy and acyloxy are optionally substituted by halogen, and wherein aryloxy is optionally substituted by halogen, alkyl, or haloalkyl; and x is 0 or 1, and wherein the compound is at least one of covalently bonded, ionically bonded, or hydrogen-bonded to the filler.

In a tenth embodiment, the present disclosure provides the treated filler of the ninth embodiment, wherein W is —Si(Y)$_x$(Z$^1$)$_{3-x}$.

In an eleventh embodiment, the present disclosure provides the treated filler of the tenth embodiment, wherein each Z$^1$ is independently hydroxyl, alkoxy, —O— covalently bonded to the surface of the filler, or —O bonded to another silicon atom to form a siloxane.

In a twelfth embodiment, the present disclosure provides the treated filler of the tenth or eleventh embodiment, wherein x is 0.

In a thirteenth embodiment, the present disclosure provides the treated filler of any one of the ninth to twelfth embodiments, wherein X is alkylene that is optionally interrupted by at least one ether, ester, carbonate, carbamate, or arylene.

In a fourteenth embodiment, the present disclosure provides the treated filler of any one of the ninth to thirteenth embodiments, wherein R is hydrogen.

In a fifteenth embodiment, the present disclosure provides the treated filler of any one of the ninth to fourteenth embodiments, wherein X is alkylene that is optionally interrupted by at least one ether, ester, carbonate, or carbamate.

In a sixteenth embodiment, the present disclosure provides the treated filler of any one of the ninth to fifteenth embodiments, wherein X is alkylene that is interrupted by —O—C(O)—NH— and optionally interrupted by —O—.

In a seventeenth embodiment, the present disclosure provides the treated filler of any one of the eighth to sixteenth embodiments, wherein the filler comprises at least one of alumina, tin oxides, antimony oxides, silica, zirconia, titania, mixed oxides of any of these, glass, or ceramics.

In an eighteenth embodiment, the present disclosure provides the treated filler of any one of the eighth to sixteenth embodiments, wherein the filler comprises at least one of mica, woolastonite, talc, or clay.

In a nineteenth embodiment, the present disclosure provides the treated filler of any one of the eighth to eighteenth embodiments, wherein the filler is a siliceous filler, calcium carbonate, or sodium metaborate.

In twentieth embodiment, the present disclosure provides the treated filler of the nineteenth embodiment, wherein Z is —O bonded to another silicon atom on a surface of the filler forming a siloxane bond with the surface.

In a twenty-first embodiment, the present disclosure provides the treated filler of the nineteenth or twentieth embodiment, wherein the siliceous filler comprises hollow glass elements.

In a twenty-second embodiment, the present disclosure provides a composition comprising a curable composition and the treated filler of any one of the eighth to twenty-first embodiments.

In a twenty-third embodiment, the present disclosure provides the composition of the twenty-second embodiment, wherein the curable composition comprises an unsaturated polyester resin.

In a twenty-fourth embodiment, the present disclosure provides the composition of the twenty-second embodiment, wherein the curable composition comprises a vinyl ester resin.

In a twenty-fifth embodiment, the present disclosure provides the composition any one of the twenty-second to twenty-fourth embodiments, further comprising at least one of styrene monomer, a substituted styrene monomer, an acrylate monomer, or a methacrylate monomer.

In a twenty-sixth embodiment, the present disclosure provides the composition of any one of the twenty-second to twenty-fifth embodiments, further comprising a free-radical initiator.

In a twenty-seventh embodiment, the present disclosure provides the composition of the twenty-sixth embodiment, wherein the free-radical initiator is an organic peroxide.

In a twenty-eighth embodiment, the present disclosure provides the composition of the twenty-sixth embodiment, wherein the free-radical initiator is a photoinitiator.

In a twenty-ninth embodiment, the present disclosure provides a method for determining degree of cure of a curable composition, the method comprising:

providing the composition of any one of the twenty-second to twenty-eighth embodiments, wherein the treated filler is present in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

In a thirtieth embodiment, the present disclosure provides the method of the twenty-ninth embodiment, wherein providing the composition comprises mixing the curable composition with the treated filler.

In a thirty-first embodiment, the present disclosure provides the method of the thirtieth embodiment, wherein mixing is carried out until the composition is uniformly colored.

In a thirty-second embodiment, the present disclosure provides a method of making a treated filler, the method comprising treating a filler with a compound represented by formula:

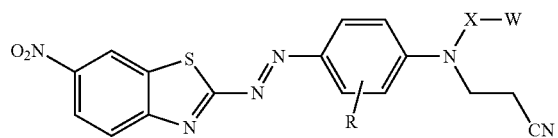

wherein

R is hydrogen or alkyl;

X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is hydroxyl, a sulfonic acid group, a phosphonic acid group, carboxylic acid, —NHR$^1$, epoxy, or —Si(Y)$_x$(Z$^1$)$_{3-x}$;

R$^1$ is hydrogen, alkyl, aryl, arylalkylenyl, or alkylarylenyl;

Y is alkyl, aryl, arylalkylenyl, or alkylarylenyl;

each Z$^1$ is independently halide, hydroxyl, alkoxy, aryloxy, acyloxy, polyalkyleneoxy, —O— bonded to another silicon atom to form a siloxane, or —O— covalently bonded to the surface of the filler, wherein alkoxy and acyloxy are optionally substituted by halogen, and wherein aryloxy is optionally substituted by halogen, alkyl, or haloalkyl; and x is 0 or 1.

In a thirty-third embodiment, the present disclosure provides the method of the thirty-second embodiment, wherein R is hydrogen.

In a thirty-fourth embodiment, the present disclosure provides the method of the thirty-second or thirty-third embodiment, wherein X is alkylene that is optionally interrupted by at least one ether, ester, carbonate, carbamate, or arylene.

In a thirty-fifth embodiment, the present disclosure provides the method of any one of the thirty-second to thirty-fourth embodiments, wherein X is alkylene that is interrupted by —O—C(O)—NH— and optionally interrupted by —O—.

In a thirty-sixth embodiment, the present disclosure provides the method of any one of the thirty-second to thirty-fifth embodiments, wherein the compound is at least one of covalently bonded, ionically bonded, or hydrogen-bonded to the filler.

In a thirty-seventh embodiment, the present disclosure provides the method comprising the compound of any one of thirty-second to thirty-sixth embodiments, wherein the filler comprises at least one of alumina, tin oxides, antimony oxides, silica, zirconia, titania, mixed oxides of any of these, glass, or ceramics.

In a thirty-eighth embodiment, the present disclosure provides the method of any one of thirty-second to thirty-sixth embodiments, wherein the filler comprises at least one of mica, woolastonite, talc, or clay.

In a thirty-ninth embodiment, the present disclosure provides the method of any one of the thirty-second to thirty-eighth embodiments, wherein the filler is a siliceous filler, calcium carbonate, or sodium metaborate.

In a fortieth embodiment, the present disclosure provides the method of the thirty-ninth embodiment, wherein the siliceous filler comprises hollow glass elements.

In a forty-first embodiment, the present disclosure provides the method of the thirty-ninth or fortieth embodiment, wherein the compound is represented by formula:

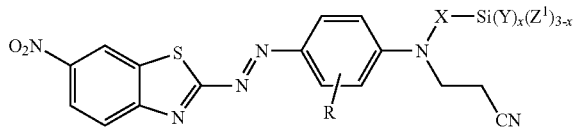

wherein
R is hydrogen or alkyl;
X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alklyene is optionally interrupted by arylene;
Y is alkyl, aryl, arylalkylenyl, or alkylarylenyl;
$Z^1$ is halide, hydroxyl, alkoxy, aryloxy, acyloxy, polyalkyleneoxy, —O— bonded to another silicon atom to form a siloxane, or —O— covalently bonded to the surface of the filler, wherein alkoxy and acyloxy are optionally substituted by halogen, and wherein aryloxy is optionally substituted by halogen, alkyl, or haloalkyl; and
x is 0 or 1.

In a forty-second embodiment, the present disclosure provides the method of the forty-first embodiment, wherein x is 0, and wherein $Z^1$ is alkoxy.

In a forty-third embodiment, the present disclosure provides the composition of the twenty-second embodiment, wherein the curable composition is an ene-thiol composition.

In order that this disclosure can be more fully understood, the following examples are set forth. It should be understood that these examples are for illustrative purposes only, and are not to be construed as limiting this disclosure in any manner.

EXAMPLES

Unless otherwise noted, all reagents were obtained or are available from fine chemical vendors, such as: Sigma-Aldrich Company, St. Louis, Mo.; EMD Millipore Chemicals, Billerica, Mass.; Alfa Aesar, Ward Hill, Mass.; J. T. Baker, Phillipsburg, N.J.; BDH Merck Ltd., Poole, Dorset, UK, and Cambridge Isotope Laboratories, Inc., Andover, Mass.; or may be synthesized by known methods. Unless otherwise reported, all ratios are by weight percent.

The following abbreviations are used to describe the examples: ° C. refers to degrees Centigrade, cm refers to centimeter, $d_6$-DMSO refers to deuterated dimethyl sulfoxide, mL refers to milliliter, mm refers to millimeter, mmol refers to millimole, μL refers to microliter, μmol refers to micromole, NMR refers to nuclear magnetic resonance, and Pa refers to Pascal.

Synthesis of 2-(4-(N-cyanoethyl-N-(2-hydroxyethyl)amino)phenylazo)-6-nitrobenzothiazole 5.00 grams (25.6 mmol) 2-amino-6-nitrobenzothiazole was added to 66 mL of a 5:1 (by volume) solution of dichloroacetic acid:acetic acid in a 250 mL flask and dissolved by heating to 50° C. for 15 minutes. The solution was cooled to 0° C. and slowly added, with constant stirring over a 10 minute period, to a 250 mL flask containing a solution of 1.94 grams (28.1 mmol) sodium nitrite in 13 mL concentrated sulfuric acid held at 0° C. After stirring for an additional 30 minutes, this solution was slowly added to a 250 mL flask containing a mixture of 4.20 grams (22.1 mmol) N-(2-cyanoethyl)-N-(2-hydroxyethyl)aniline in 13 mL acetic acid, also held at 0° C., and stirred for 1 hour. The reaction mixture was then neutralized by the addition of a saturated aqueous sodium carbonate solution until the pH of the reaction mixture was approximately 7. The resulting precipitate was isolated by vacuum filtration. The precipitate was dissolved in 200 mL methylene chloride, then dried by passing through a bed of anhydrous sodium sulfate, filtered, and condensed in a rotary evaporator. The resulting solid was further purified by loading onto a 3 by 23 cm silica gel column, then eluting with an acetone:methylene chloride solution where the solvent ratio, by volume, was gradually changed from 10:90 to 30:70. Subsequent fractions containing the pure compound were combined, condensed under reduced pressure and dried under a vacuum of 0.3 mm mercury (40.0 Pa) at approximately 21° C. to yield 4.30 grams of a purple solid, subsequently confirmed by NMR spectroscopy to be 2-(4-(N-cyanoethyl-N-(2-hydroxyethyl)amino)phenylazo)-6-nitrobenzothiazole [$^1$H NMR (500 MHz, $d_6$-DMSO) δ 9.07 (dd, J=0.4, 2.4 Hz, 1H), 8.32 (dd, J=2.4, 8.9 Hz, 1H), 8.17 (dd, J=0.4, 8.9 Hz, 1H), 7.91 (d, J=9.4 Hz, 2H), 7.11 (d, J=9.4 Hz, 2H), 4.99 (t, J=5.1 Hz, 1H), 3.95 (t, J=7.1 Hz, 2H), 3.73-3.65 (m, 4H), 2.91 (t, J=6.9 Hz, 2H)].

Synthesis of [3-(triethoxysilyl)propyl]-carbamic acid 2-{(2-cyanoethyl)-[4-(6-nitrobenzo-thiazol-2-ylazo)-phenyl]amino}-ethyl ester

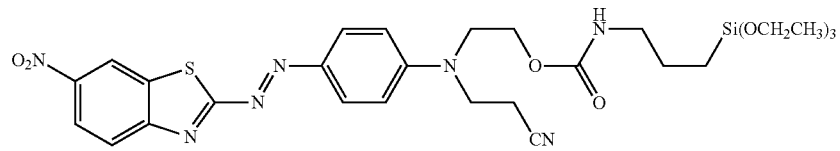

140 μL (567 μmol) of 3-(triethoxysilyl)propyl isocyanate was added to a 25 mL flask containing a solution of 0.2012 g (508 μmol) 2-(4-(N-cyanoethyl-N-(2-hydroxyethyl)amino)-phenylazo)-6-nitrobenzothiazole in 10 mL dimethylsulfoxide. This reaction mixture was heated to 75° C. and stirred under a nitrogen atmosphere for 72 hours at this temperature, after which 1 mL of the reaction product was used to treat the glass bubbles as described in Example 1.

Synthesis of 3-[4-(2-{(2-cyanoethyl)-[4-(6-nitro-benzothiazol-2-ylazo)-phenyl]-amino}-ethoxy)-phenyl]-propionic acid methyl ester

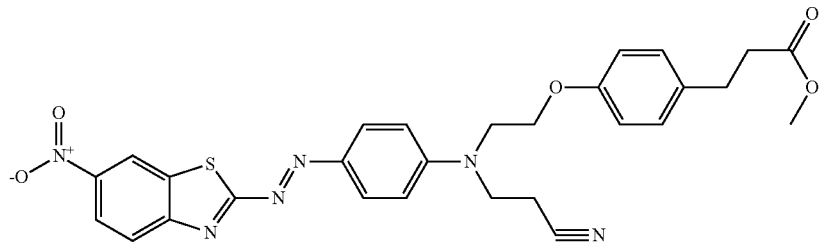

0.151 g (381 µmol) 3-{2-hydroxyethyl)-[4-(6-nitro-benzothiazol-2-ylazo)-phenyl]-amino}-propionitrile, 64.4 mg (357 µmol) methyl 3-(4-hydroxyphenyl)-propionate and 0.117 g (446 µmol) triphenylphosphine were dissolved in 10 mL of tetrahydrofuran (THF) in a 50 mL flask at approximately 21° C. This solution was cooled to 0° C. by placing the flask in an ice/water bath. The flask was equipped with an addition funnel containing a solution of 110 µL (559 µmol) diisopropyl azodicarboxylate (DIAD) in 5 mL of THF. The DIAD/THF solution was added dropwise to the stirred reaction mixture over a period of 2 hours under an atmosphere of nitrogen while the temperature was maintained at approximately 0° C. When the addition was complete, the reaction mixture was allowed to warm to approximately 21° C. The reaction mixture was then stirred under an atmosphere of nitrogen for 20 hours at approximately 21° C. The reaction mixture was condensed in a rotary evaporator. The resulting material was partitioned between water (approximately 50 mL) and methylene chloride ($CH_2Cl_2$) (approximately 50 mL). The organic layer was then removed, and the aqueous layer was extracted twice more with $CH_2Cl_2$ (approximately 50 mL each time). The organic layers were combined, dried by passing through a bed of anhydrous sodium sulfate, filtered, and condensed in a rotary evaporator. The resulting solid was further purified by loading onto a 4 by 32 cm silica gel column, then eluting with approximately 10:90 (by volume) ethyl acetate:methylene chloride solution. Subsequent fractions containing the pure compound were combined, condensed under reduced pressure and then dried under vacuum of 0.3 mm mercury (40.0 Pa) at approximately 21° C. to yield 73.7 mg of a solid subsequently confirmed by NMR spectroscopy to be 3-[4-(2-{(2-cyanoethyl)-[4-(6-nitro-benzothiazol-2-ylazo)-phenyl]-amino}-ethoxy)-phenyl]-propionic acid methyl ester [$^1$H NMR (500 MHz, CDCl$_3$) δ 8.72 (d, J=2.4 Hz, 1H), 8.29 (dd, J=2.4, 8.8 Hz, 1H), 8.12 (d, J=8.8 Hz, 1H), 8.00 (m, 2H), 7.11 (m, 2H), 6.82 (m, 2H), 6.79 (m, 2H), 4.20 (t, J=5.0 Hz, 2H), 4.00 (t, J=5.0 Hz, 2H), 3.99 (t, J=7.1 Hz, 2H), 3.63 (s, 3H), 2.87 (t, J=7.6 Hz, 2H), 2.81 (t, J=7.1 Hz, 2H), 2.57 (t, J=7.6 Hz, 2H)].

Synthesis of 3-[4-(2-{(2-cyanoethyl)-[4-(6-nitro-benzothiazol-2-ylazo)-phenyl]-amino}-ethoxy)-phenyl]-propionic acid

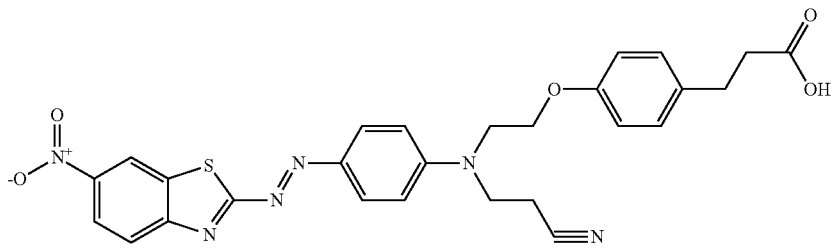

A 3.6 mg/mL lithium hydroxide (LiOH) in water solution was prepared by dissolving 71.9 mg of LiOH in 20 mL of deionized water. In a 20 mL vial, 56.7 mg (102 µmol) 3-[4-(2-{(2-cyanoethyl)-[4-(6-nitro-benzothiazol-2-ylazo)-phenyl]-amino}-ethoxy)-phenyl]-propionic acid methyl ester were dissolved in 4 mL of THF at approximately 21° C. 1.09 mL of the aqueous LiOH solution was added to the vial containing the methyl ester dye/THF solution. This vial was capped and the contents mixed in a mechanical shaker, model "WRIST ACTION SHAKER MODEL 75" from Burrell Scientific (Pittsburgh, Pa.) for 3 hours at approximately 21° C. The reaction mixture was condensed in a rotary evaporator. The resulting material was partitioned between 0.1 N aqueous hydrogen chloride (HCl) (approximately 25 mL) and $CH_2Cl_2$ (approximately 25 mL). The organic layer was then removed, and the aqueous layer was extracted twice more with $CH_2Cl_2$ (approximately 25 mL each time). The organic layers were combined, dried by passing through a bed of anhydrous sodium sulfate, filtered, and condensed in a rotary evaporator. The resulting solid was dried under vacuum of 0.3 mm mercury (40.0 Pa) at approximately 21° C. to yield 48.7 mg of a solid subsequently confirmed by NMR spectroscopy to be 3-[4-(2-{(2-cyanoethyl)-[4-(6-nitro-benzothiazol-2-ylazo)-phenyl]-amino}-ethoxy)-phenyl]-propionic acid [$^1$H NMR (500 MHz, d-6 acetone) δ 8.95 (d, J=2.5 Hz, 1H), 8.35 (dd, J=2.5, 8.8 Hz, 1H), 8.17 (d, J=8.8 Hz, 1H), 7.98 (m, 2H), 7.21 (m, 2H), 7.17 (m, 2H), 6.88 (m, 2H), 4.32 (t, J=5.4 Hz, 2H), 4.16

(t, J=5.4 Hz, 2H), 4.15 (t, J=7.1 Hz, 2H), 3.00 (t, J=7.1 Hz, 2H), 2.82 (t, J=7.6 Hz, 2H), 2.54 (t, J=7.6 Hz, 2H)].

Example 1

0.9759 grams of glass bubbles, obtained under the trade designation "GLASS BUBBLES S15" from 3M Company (St. Paul, Minn.) were added to a 100 mL round bottomed flask containing 20 mL deionized water, and the suspension was stirred for 10 minutes at 21° C. The glass bubbles were then isolated by vacuum filtration and washed with 10 mL of deionized water, followed by 50 mL of ethanol. 1 mL of [3-(triethoxysilyl)propyl]-carbamic acid 2-{(2-cyanoethyl)-[4-(6-nitrobenzo-thiazol-2-ylazo)-phenyl]amino}ethyl ester was added to a 20 mL glass vial followed by 5 mL of a 95% by volume aqueous ethanol solution and mixed in a mechanical shaker, model "WRIST ACTION SHAKER MODEL 75" from Burrell Scientific (Pittsburgh, Pa.) for 5 minutes at 21° C. The vial was removed from the shaker, the washed glass bubbles added, and the vial returned to the shaker for 2 hours. The resulting dyed glass bubbles were then isolated by vacuum filtration, washed with 50 mL ethanol followed by sufficient acetone until the eluent was essentially colorless. The resulting pink glass bubbles were allowed to air dry at 21° C. for 18 hours. 0.30 grams of the dyed glass bubbles were uniformly mixed into 10.0 grams of a white automotive body filler that had been dispensed from the cartridge of a body filler kit, obtained under the trade designation "3M PREMIUM BODY FILLER, PART No. 50597" from 3M Company. The resulting body filler was pink. 0.21 grams of a white 50% benzoyl peroxide hardener paste, obtained under the trade designation "BENOX B-50" from Syrgis Performance Initiators, Inc. (Helena, Ark.) was then uniformly mixed on a palette for 45 seconds at 21° C. with the pink body filler. After 12 minutes, a hardened white body filler was obtained with no residual pink color.

Example 2

A 2.1 mg/mL solution of 3-[4-(2-{(2-cyanoethyl)-[4-(6-nitro-benzothiazol-2-ylazo)-phenyl]-amino}-ethoxy)-phenyl]-propionic acid in acetone was prepared by dissolving 8.2 mg of 3-[4-(2-{(2-cyanoethyl)-[4-(6-nitro-benzothiazol-2-ylazo)-phenyl]-amino}-ethoxy)-phenyl]-propionic acid in 4.0 mL of acetone. 0.3020 grams of ultrafine uncoated calcium carbonate, obtained under the trade designation "SOCAL 31" from Solvay Chemicals, Inc. (Brussels, Belgium), were added to a 20 mL vial containing a solution prepared by adding 300 µL of the 2.1 mg/mL solution of 3-[4-(2-{(2-cyanoethyl)-[4-(6-nitro-benzothiazol-2-ylazo)-phenyl]-amino}-ethoxy)-phenyl]-propionic acid in acetone to 1.7 mL of acetone. The vial was capped and the contents mixed in a mechanical shaker, model "WRIST ACTION SHAKER MODEL 75" from Burrell Scientific (Pittsburgh, Pa.) for 2 hours at approximately 21° C. The resulting dyed calcium carbonate was isolated by vacuum filtration and washed with sufficient acetone until the eluent was essentially colorless. The resulting pinkish-purple calcium carbonate powder was dried under vacuum of 0.3 mm mercury (40.0 Pa) at approximately 70° C. for 2 hours. 39.6 mg of the dyed calcium carbonate powder were uniformly mixed into 5.15 grams of a white automotive body filler that had been dispensed from the cartridge of a body filler kit, obtained under the trade designation "3M PREMIUM BODY FILLER, PART No. 50597" from 3M Company. The resulting body filler was pink. 0.120 grams of a white 50% benzoyl peroxide hardener paste, obtained under the trade designation 'BENOX B-50" from Syrgis Performance Initiators, Inc. (Helena, Ark.) was then uniformly mixed on a palette for 60 seconds at 21° C. with the pink body filler. After 12 minutes, a hardened white body filler was obtained with no residual pink color.

Example 3

A 2.1 mg/mL solution of 3-[4-(2-{(2-cyanoethyl)-[4-(6-nitro-benzothiazol-2-ylazo)-phenyl]-amino}-ethoxy)-phenyl]-propionic acid in acetone was prepared by dissolving 8.2 mg of 3-[4-(2-{(2-cyanoethyl)-[4-(6-nitro-benzothiazol-2-ylazo)-phenyl]-amino}-ethoxy)-phenyl]-propionic acid in 4.0 mL of acetone. 0.2997 grams of granular sodium metaborate hydrate, obtained from Sigma-Aldrich, Company (St. Louis, Mo.), were added to a 20 mL vial containing a solution prepared by adding 600 µL of the 2.1 mg/mL solution of 3-[4-(2-{(2-cyanoethyl)-[4-(6-nitro-benzothiazol-2-ylazo)-phenyl]-amino}-ethoxy)-phenyl]-propionic acid in acetone to 1.4 mL of acetone. The vial was capped and the contents mixed in a mechanical shaker, model "WRIST ACTION SHAKER MODEL 75" from Burrell Scientific (Pittsburgh, Pa.) for 2 hours at approximately 21° C. The resulting dyed sodium metaborate was isolated by vacuum filtration and washed with sufficient acetone until the eluent was essentially colorless. The resulting pinkish-purple sodium metaborate granules were dried under vacuum of 0.3 mm mercury (40.0 Pa) at approximately 70° C. for 2 hours. A mortar and pestle were used to grind the dyed sodium metaborate granules into a fine powder. 21.7 mg of the dyed sodium metaborate powder were uniformly mixed into 5.01 grams of a white automotive body filler that had been dispensed from the cartridge of a body filler kit, obtained under the trade designation "3M PREMIUM BODY FILLER, PART No. 50597" from 3M Company. The resulting body filler was pink. 0.125 grams of a white 50% benzoyl peroxide hardener paste, obtained under the trade designation 'BENOX B-50" from Syrgis Performance Initiators, Inc. (Helena, Ark.) were then uniformly mixed on a palette for 60 seconds at 21° C. with the pink body filler. After 12 minutes, a hardened white body filler was obtained with no residual pink color.

Various modifications and alterations of this disclosure may be made by those skilled in the art without departing from the scope and spirit of the disclosure, and it should be understood that this invention is not to be unduly limited to the illustrative embodiments set forth herein.

What is claimed is:
1. A treated filler comprising:
   an inorganic filler having on at least a portion of its surface a compound of formula

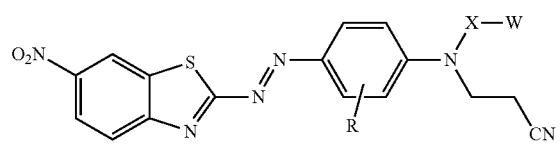

wherein
   R is hydrogen or alkyl;
   X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is —Si(Y)$_x$(Z$^1$)$_{3-x}$;

Y is alkyl, aryl, arylalkylenyl, or alkylarylenyl;

each Z$^1$ is independently halide, hydroxyl, alkoxy, aryloxy, acyloxy, polyalkyleneoxy, —O— covalently bonded to the surface of the inorganic filler, or —O— bonded to another silicon atom to form a siloxane, wherein alkoxy and acyloxy are optionally substituted by halogen, and wherein aryloxy is optionally substituted by halogen, alkyl, or haloalkyl; and x is 0 or 1, and wherein the compound is at least one of covalently bonded, ionically bonded, or hydrogen-bonded to the inorganic filler.

2. The treated filler of claim 1, wherein the inorganic filler is a siliceous filler, calcium carbonate, or sodium metaborate.

3. The treated filler of claim 1, wherein W is —Si(Y)$_x$(Z$^1$)$_{3-x}$, wherein x is 0, and wherein each Z$^1$ is independently hydroxyl, alkoxy, —O— covalently bonded to the surface of the inorganic filler, or —O bonded to another silicon atom to form a siloxane.

4. The treated filler of claim 1, wherein X is alkylene that is optionally interrupted by at least one ether, ester, carbonate, carbamate, or arylene.

5. The treated filler of claim 1, wherein X is alkylene that is interrupted by —O—C(O)—NH— and optionally interrupted by —O—.

6. The treated filler of claim 1, wherein R is H.

7. The treated filler of claim 1, wherein the inorganic filler comprises at least one of alumina, tin oxides, antimony oxides, silica, zirconia, titania, glass, or ceramics.

8. The treated filler of claim 1, wherein the inorganic filler comprises hollow glass elements.

9. A composition comprising a curable polymeric resin and the treated filler of claim 1.

10. The composition of claim 9, further comprising a free radical initiator.

11. The composition of claim 10, wherein the free-radical initiator is an organic peroxide.

12. The composition of claim 9, wherein the composition further comprises at least one of styrene monomer, a substituted styrene monomer, an acrylate monomer, or a methacrylate monomer.

13. A method of making the treated filler of claim 1, the method comprising treating the inorganic filler with the compound represented by formula:

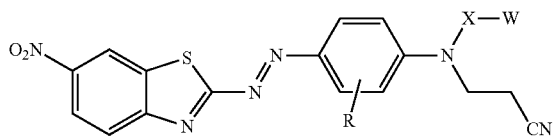

wherein
R is hydrogen or alkyl;
X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is —Si(Y)$_x$(Z$^1$)$_{3-x}$;

Y is alkyl, aryl, arylalkylenyl, or alkylarylenyl;

each Z$^1$ is independently halide, hydroxyl, alkoxy, aryloxy, acyloxy, polyalkyleneoxy, —O— covalently bonded to the surface of the inorganic filler, or —O— bonded to another silicon atom to form a siloxane, wherein alkoxy and acyloxy are optionally substituted by halogen, and wherein aryloxy is optionally substituted by halogen, alkyl, or haloalkyl; and x is 0 or 1.

14. A composition comprising a curable polymeric resin and a treated filler, wherein the curable polymeric resin is curable by free-radical polymerization, wherein the treated filler comprises:

a filler having on at least a portion of its surface a compound of formula

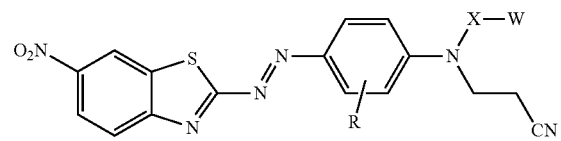

wherein
R is hydrogen or alkyl;
X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is hydroxyl, a sulfonic acid group, a phosphonic acid group, carboxylic acid group, —NHR$^1$, epoxy, or —Si(Y)$_x$(Z$^1$)$_{3-x}$;

R$^1$ is hydrogen, alkyl, aryl, arylalkylenyl, or alkylarylenyl;

Y is alkyl, aryl, arylalkylenyl, or alkylarylenyl;

each Z$^1$ is independently halide, hydroxyl, alkoxy, aryloxy, acyloxy, polyalkyleneoxy, —O— covalently bonded to the surface of the filler, or —O— bonded to another silicon atom to form a siloxane, wherein alkoxy and acyloxy are optionally substituted by halogen, and wherein aryloxy is optionally substituted by halogen, alkyl, or haloalkyl; and x is 0 or 1, and wherein the compound is at least one of covalently bonded, ionically bonded, or hydrogen-bonded to the filler.

15. The composition of claim 14, further comprising a free radical initiator.

16. The composition of claim 15, wherein the free-radical initiator is an organic peroxide.

17. The composition of claim 14, wherein the composition further comprises at least one of styrene monomer, a substituted styrene monomer, an acrylate monomer, or a methacrylate monomer.

18. The composition of claim 14, wherein the inorganic filler comprises at least one of alumina, tin oxides, antimony oxides, silica, zirconia, titania, glass, or ceramics.

19. The composition of claim 14, wherein the inorganic filler is a siliceous filler, calcium carbonate, or sodium metaborate.

20. The composition of claim 14, wherein X is alkylene that is optionally interrupted by at least one ether, ester, carbonate, carbamate, or arylene.

21. The composition of claim 14, wherein the inorganic filler comprises hollow glass elements.

22. A method for determining degree of cure of a curable polymeric resin, the method comprising:
providing the composition of claim 15, wherein the treated filler is present in an amount sufficient to provide the composition with a first absorbance at a wavelength in a range from 400 nanometers to 700 nanometers; and
allowing the composition to cure to provide a cured composition, wherein the cured composition has a second absorbance at the wavelength that is different from the first absorbance.

23. A composition comprising an unsaturated polyester resin and a treated filler, wherein the treated filler comprises:
a filler having on at least a portion of its surface a compound of formula

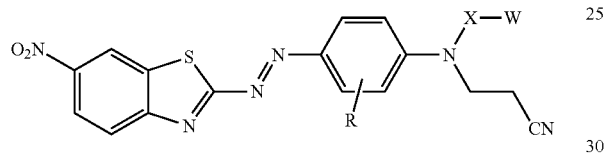

wherein

R is hydrogen or alkyl;

X is alkylene, arylalkylene, or alkylarylene, wherein alkylene, arylalkylene, and alkylarylene are optionally interrupted by at least one of an ether, thioether, amine, amide, ester, thioester, carbonate, thiocarbonate, carbamate, thiocarbamate, urea, or thiourea, and wherein alkylene is optionally interrupted by arylene;

W is hydroxyl, a sulfonic acid group, a phosphonic acid group, carboxylic acid group, $-NHR^1$, epoxy, or $-Si(Y)_x(Z^1)_{3-x}$;

$R^1$ is hydrogen, alkyl, aryl, arylalkylenyl, or alkylarylenyl;

Y is alkyl, aryl, arylalkylenyl, or alkylarylenyl;

each $Z^1$ is independently halide, hydroxyl, alkoxy, aryloxy, acyloxy, polyalkyleneoxy, —O— covalently bonded to the surface of the filler, or —O— bonded to another silicon atom to form a siloxane, wherein alkoxy and acyloxy are optionally substituted by halogen, and wherein aryloxy is optionally substituted by halogen, alkyl, or haloalkyl; and x is 0 or 1, and wherein the compound is at least one of covalently bonded, ionically bonded, or hydrogen-bonded to the filler.

* * * * *